(12) United States Patent
Lehtinen

(10) Patent No.: US 8,012,101 B2
(45) Date of Patent: Sep. 6, 2011

(54) PUNCHING TOOL FOR TAKING BIOLOGICAL SAMPLES

(75) Inventor: Kauko Lehtinen, Raisio (FI)

(73) Assignee: Wallac Oy, Turku (FI)

( * ) Notice: Subject to any disclaimer, the term of this patent is extended or adjusted under 35 U.S.C. 154(b) by 868 days.

(21) Appl. No.: 11/791,338

(22) PCT Filed: Nov. 23, 2005

(86) PCT No.: PCT/FI2005/050430
§ 371 (c)(1),
(2), (4) Date: May 23, 2007

(87) PCT Pub. No.: WO2006/056658
PCT Pub. Date: Jun. 1, 2006

(65) Prior Publication Data
US 2007/0293789 A1 Dec. 20, 2007

(30) Foreign Application Priority Data
Nov. 24, 2004 (FI) ...................................... 20045456

(51) Int. Cl.
*A61B 10/00* (2006.01)
*A61B 17/14* (2006.01)
*A61B 17/32* (2006.01)
(52) U.S. Cl. ......... 600/564; 600/562; 600/567; 606/184
(58) Field of Classification Search .......... 600/562–572; 606/167–170, 172, 184, 185
See application file for complete search history.

(56) References Cited

U.S. PATENT DOCUMENTS
2,013,758 A * 9/1935 Livermore ...................... 72/330
(Continued)

FOREIGN PATENT DOCUMENTS
DE 39 42 170 A1 7/1991
(Continued)

OTHER PUBLICATIONS
International Search Report dated Mar. 6, 2006.
(Continued)

*Primary Examiner* — Jeffrey G Hoekstra
(74) *Attorney, Agent, or Firm* — Buchanan Ingersoll & Rooney PC

(57) ABSTRACT

The invention relates to a punching tool for taking a biological sample from a filter using punching, the punching tool comprising a punch and a die provided with a punching channel for conveying the sample from the upper surface of the die towards the lower end of the die that includes a guidance means of the sample comprising a guidance channel arranged as an extension of the punching channel for receiving the sample from the punching channel, the diameter of the guidance channel is 1.02 to 2× the diameter of the punch and is greater than the diameter of the punching channel, and at the connecting point with the punching channel the guidance channel forms a shoulder and broadens towards the free end of the guidance means. In order to reduce the number of mistakes when taking samples, while the structure of the punching tool still remains simple at the end of the guidance means that faces towards the punching channel of the die, the diameter of the guidance channel is constant at a portion of the length thereof and the walls of the shoulder are placed at an angle from 170 to 300 degrees in relation to one another.

20 Claims, 4 Drawing Sheets

U.S. PATENT DOCUMENTS

| | | | |
|---|---|---|---|
| 5,062,308 A | 11/1991 | Rising et al. | |
| 5,146,794 A | 9/1992 | Rising et al. | |

FOREIGN PATENT DOCUMENTS

| | | |
|---|---|---|
| EP | 0 583 078 A2 | 2/1994 |
| JP | 10-230329 A | 9/1998 |
| JP | 2002-307388 A | 10/2002 |

OTHER PUBLICATIONS

Written Opinion of the International Searching Authority dated Mar. 1, 2006.

Finnish Search Report dated May 11, 2005 (with English translation of category of cited documents).

* cited by examiner

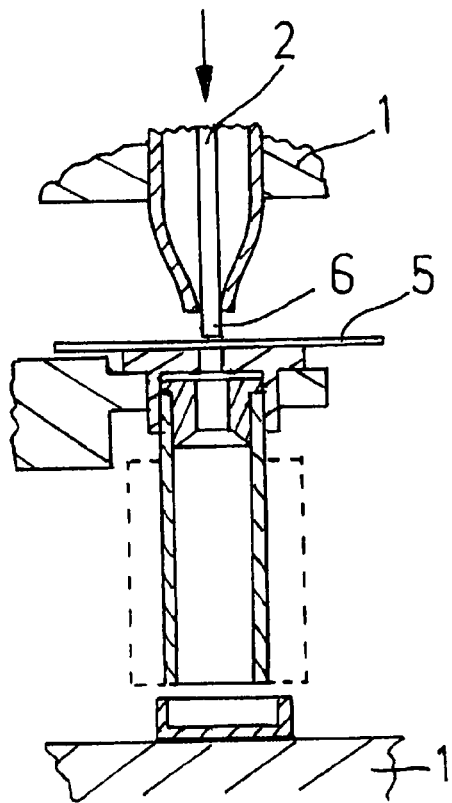
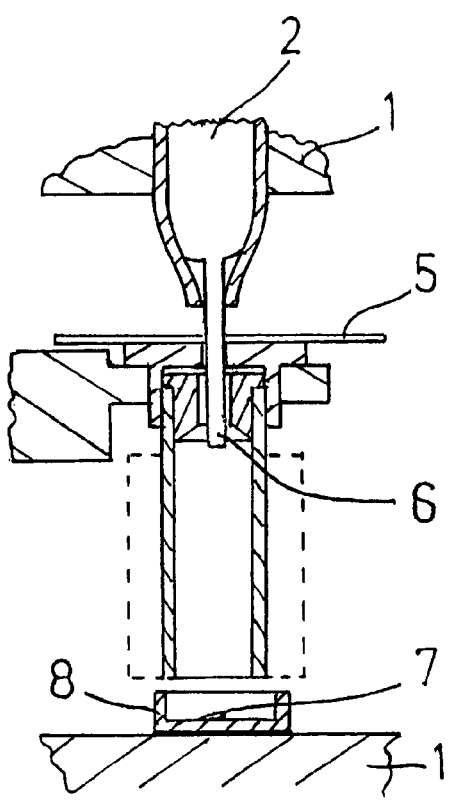
FIG. 6     FIG. 7
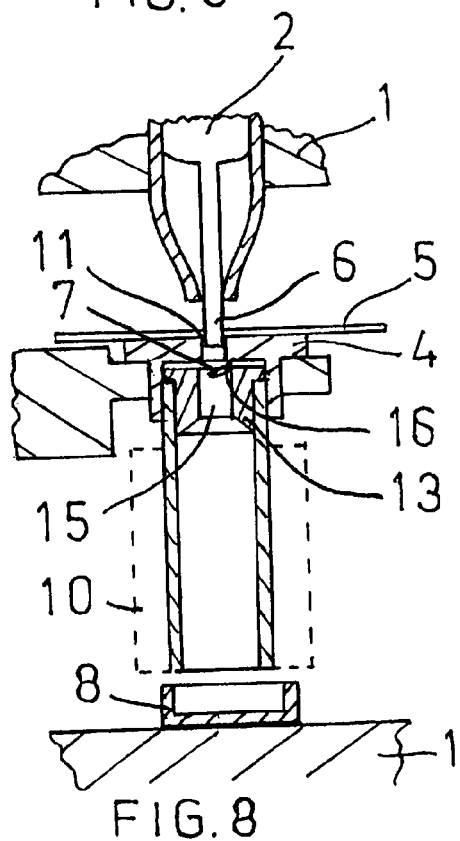
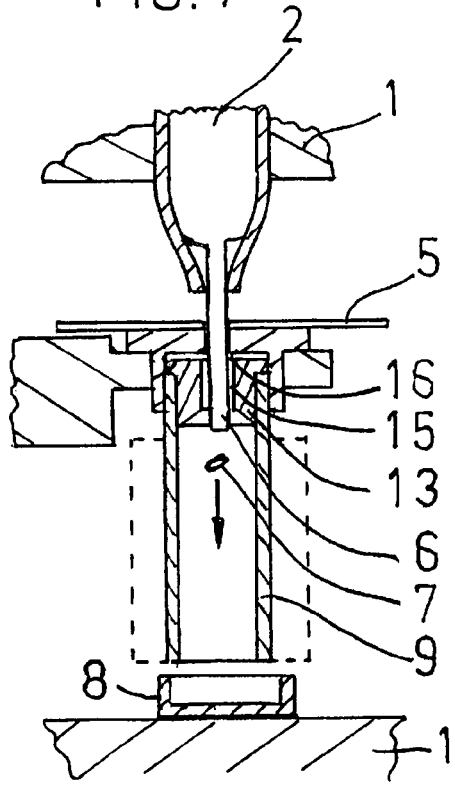
FIG. 8     FIG. 9

PUNCHING TOOL FOR TAKING BIOLOGICAL SAMPLES

BACKGROUND OF THE INVENTION

The invention relates to a punching tool for taking a biological sample from a filter using punching, the punching tool comprising a punch and a die provided with a punching channel for conveying the sample from the upper surface of the die to the lower end of the die. More precisely, the invention relates to a punching tool also provided with a guidance means of the sample that comprises a guidance channel arranged as an extension of the punching channel for receiving the sample from the punching channel, the diameter of the guidance channel is 1.02 to 2× the diameter of the punch and is greater than the diameter of the punching channel, and at the connecting point with the punching channel the guidance channel forms a shoulder and broadens towards the free end of the guidance means. In this context the diameter of the punch naturally refers to the diameter of the cutting end of the punch.

Publication DE 3942170 discloses such an instrument for taking paper samples in order to determine the basis weight (grammage) of paper.

A punching tool is known in the art for taking a biological sample that comprises a punch and a die provided with a punching channel for conveying the sample from the upper surface of the die towards the lower end of the die. Such an instrument can be used to take blood samples, saliva samples, tissue fluid samples and other body fluid samples. The filter is typically a planar sheet made of fibrous material such as paperboard, cardboard or paper, from which several samples with a small diameter can be taken. The diameter of the sample typically ranges from 0.8 to 3.2 mm. The shape of the samples is generally circular, and can therefore be referred to as discoidal. The sample is transferred from the instrument to a small vessel placed beneath it, when the sample has successfully been punched from the sheet. The vessel is a small cup that can easily be delivered to the laboratory where the sample will be analysed. There may be dozens of vessels adjacently attached to one another, thus forming a structure that resembles a square when seen from above.

A problem with the instrument intended to be used for taking a biological sample is that the sample is not necessarily always released from the instrument. This is due to the fact that the edges of the sample include fluff originating from the fibres in the filter that may adhere to the different parts of the instrument. When taking biological samples it is known to register the release of a sample, and therefore the punching can be repeated if required, meaning that another punching may be performed, if the punching tool has not registered the release of the sample and a successful punching. However, a new punching does not necessarily lead to the desired result, instead each hundredth sample remains adhered to the instrument, from where it may eventually with time be released and fall into an incorrect vessel. Such a mistake does not only decelerate sample taking but also causes the sample to be registered into an incorrect vessel, which may relate to an incorrect person or animal. It is obvious that such a mistake may have fatal consequences.

The punching tool should at times be disassembled and cleaned. The disassembling and cleaning should be carried out more frequently, the more mistakes occur during punching.

BRIEF DESCRIPTION OF THE INVENTION

It is an object of the invention to provide a punching tool for taking biological samples that by simple means offers an instrument for use that allows carrying out an extremely safe sampling and thus considerably reducing the generation of mistakes.

In order to achieve the object the punching tool is characterized in that at the end of the guidance means facing towards the punching channel of the die the diameter of the guidance channel is constant at a portion of the length thereof and that the walls of the shoulder are at an angle ranging from 170 to 300 degrees in relation to one another.

It is to be assumed that the guidance channel should be provided with a minimum length in order for the punching tool to operate as desired. Owing to the above it is preferable that the diameter of the guidance channel remains constant for a length of at least 2 mm of the guidance channel.

The more the angle goes below the value 180 degrees the more uncertain it becomes that the sample will be released from the punching tool as desired.

The guidance channel preferably widens conically in such a manner that the cone angle ranges between 50 and 100 degrees. Such a widening improves the probability of a successful sample taking.

It is of great advantage that the smoothness of the surface in the guidance channel corresponds to a polished surface, this further assisting the sample to be released from the punching tool.

When the tip of the punch is further arranged to be moved a distance at least 2 mm past the free end of the guidance means, then the push of the punch most probably releases the sample from the punching tool.

Preferred embodiments of the punching tool according to the invention are disclosed in the accompanying claims 2 to 12.

A significant advantage of the punching tool according to the invention is that it considerably reduces the number of mistakes when taking samples even though the structure thereof is simple. On account of the guidance means of the punching tool the number of mistakes has been reduced to a tenth and even much more in comparison with an instrument, in which the guidance means is not included. The guidance means also allows reducing the need to service the instrument.

BRIEF DESCRIPTION OF THE DRAWINGS

In the following the invention will be explained in greater detail by means of a preferred embodiment thereof with reference to the accompanying drawing, in which FIGS. 6 to 9 illustrate the operation of the punching tool shown in FIG. 4.

DETAILED DESCRIPTION OF THE INVENTION

Figure 1:
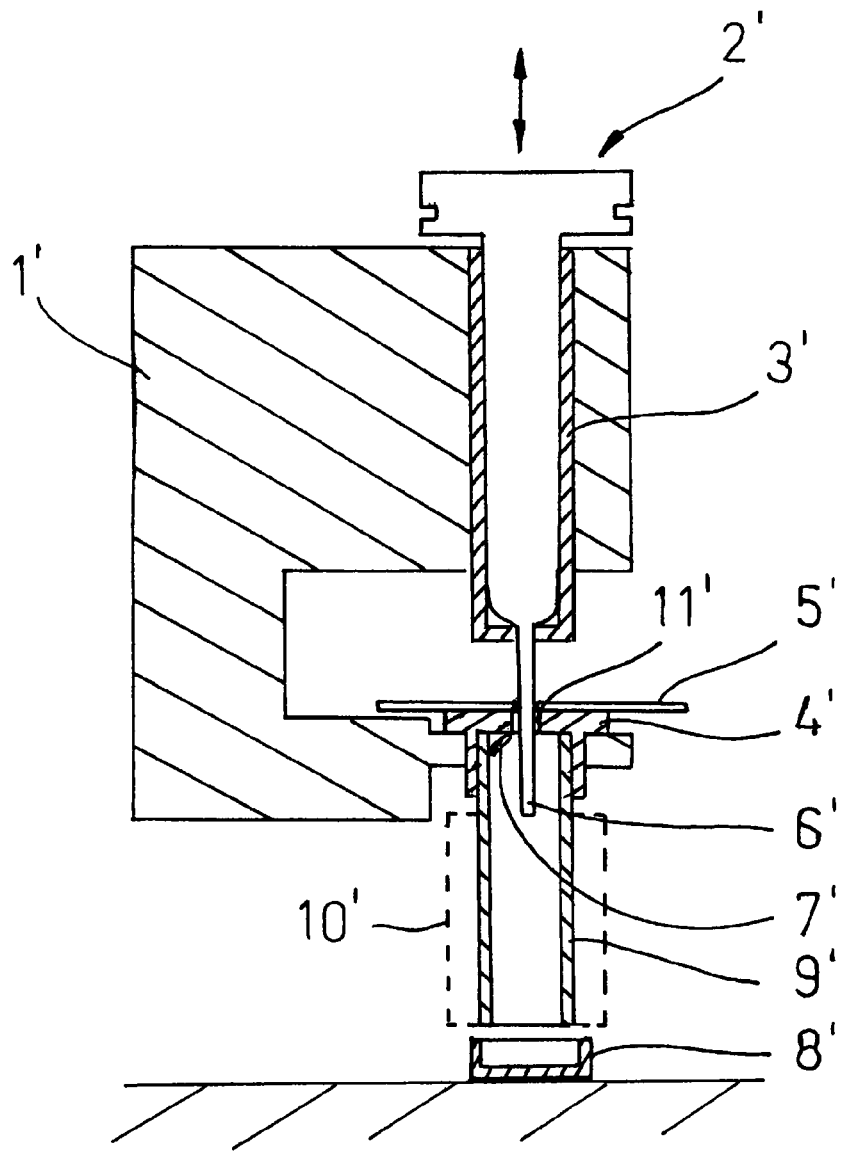
FIG. 1 shows a side view of a known punching tool in cross section.

FIG. 1 shows a side view in cross section of a punching tool for taking a biological sample representing the prior art. The instrument comprises a frame 1' and a punch supported by the frame, said punch generally being referred to with reference numeral 2'. The punch 2' resembling a symmetric body of revolution is arranged within a tubular guidance means 3' and to be movable upwards and downwards in respect of the latter, which is indicated by the double arrow in the Figure. In FIG. 1 the punch 2' is in the lowest position thereof. Reference numeral 4' refers to a die of the punching tool supported by the frame 1'. A filtering paper 5' is placed on the upper surface of the die 4', on which filtering paper one or more biological samples are absorbed, from which one or more samples are taken. The die 4' comprises a punching channel 11' that determines the size of the diameter of the sample.

In FIG. 1 the tip 6' of the punch has punched a discoidal sample 7' from the filtrating paper 5', which has adhered to the lower surface 4' of the die. FIG. 1 thus shows the mistake, or the situation, in which the punching tool has not been able to transfer as desired the sample 7' into a vessel 8' shaped as a sample cup and placed beneath the punching tool. Reference numeral 9' indicates a shaft tube that prevents the falling sample 7' from missing the sample cup 8'. The dashed line shows a recording device 10' surrounding the shaft tube 9' that registrates through light changes whether the sample has fallen into the sample cup 8' or not. The light source of the recording device 10' is a LED component, for example. The shaft tube 9' thus also operates as a support for the recording device 10'.

Even though the punch 2' of the punching tool shown in FIG. 1 were to perform repetitive strokes through the punching channel 11' of the die 4' the sample 7' would not be released from the die.

Figure 2:
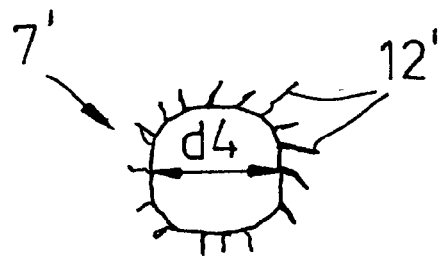
FIGS. 2 and 3 show a top view and correspondingly a side view of a sample taken with the punching tool.
Figure 3:
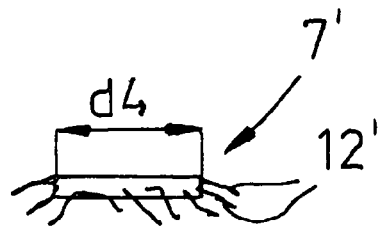

FIGS. 2 and 3 show an enlarged view of a sample 7' having a diameter of d4=1.2 mm. What can be observed is that the edges of the sample 7' are provided with fluffs 12'. The fluffs 12' originate from the fibres in the filtering paper. The length of the fluffs 12' varies; the longest ones may exceed one millimeter, thus corresponding approximately to the diameter d4 of the sample 7'. The fluffs 12' cause the sample 7' to incorrectly adhere to the die 4' of the punching tool shown in FIG. 1. The fluffs 12' may therefore adhere to the die 4' in such a manner that a new stroke with the punch 2' will not release the sample 7' from the die but turns this to the side, in which case repeated strokes of the punch are unable to release the sample 7'. Static electricity may provide a reason for the fact that the sample 7' is adhered to the die 4'.

Figure 4:
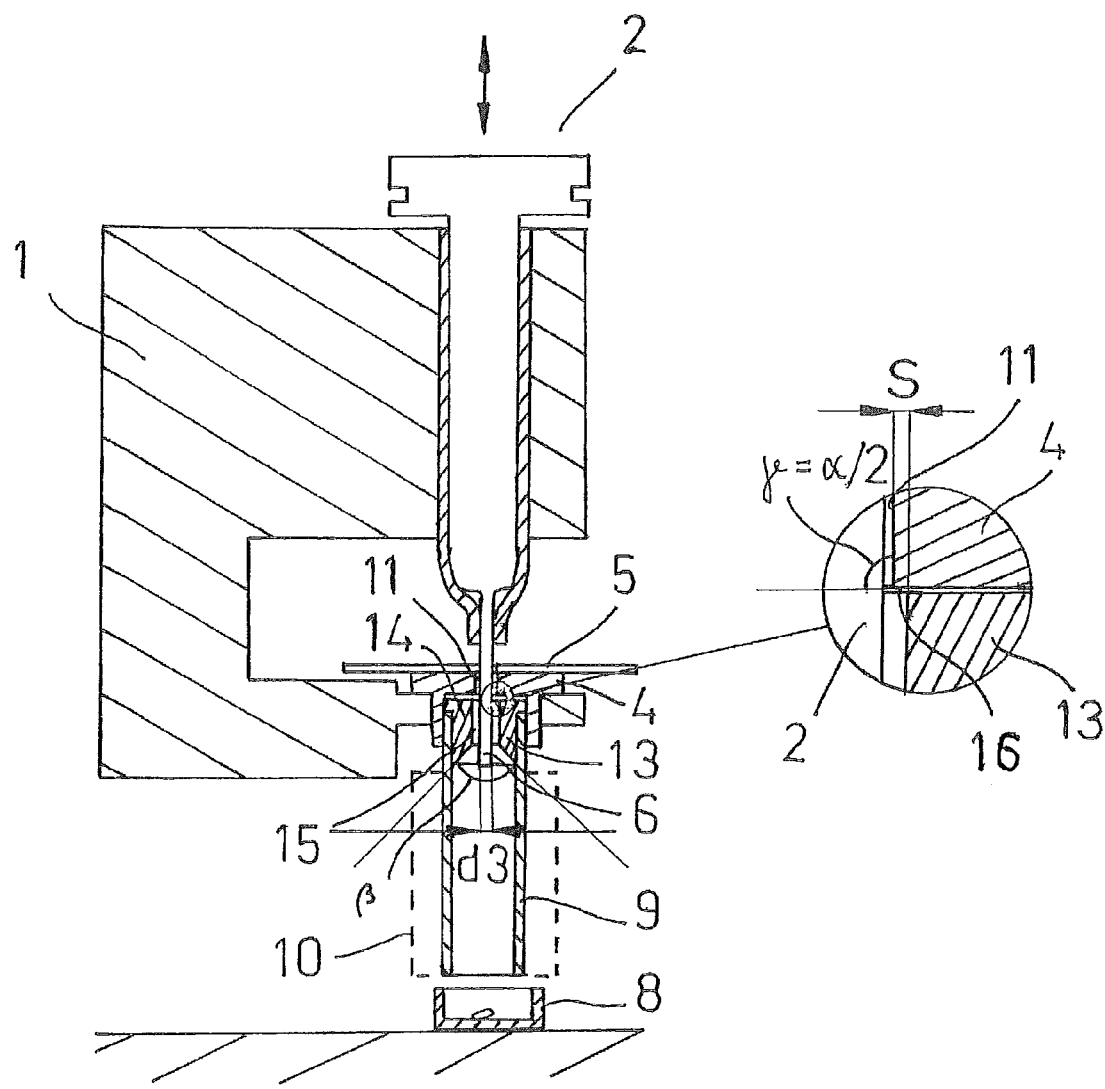
FIG. 4 shows a side view of a punching tool according to the invention in cross section.

FIG. 4 shows a punching tool according to the invention. Corresponding reference numerals have been used in the Figure for the corresponding parts shown in FIG. 1.

The punching tool shown in FIG. 4 differs from the punching tool shown in FIG. 1 in that a guidance means 13 is arranged beneath the die 4. Owing to the guidance means 13 the sample 7 to be taken from the filtering material cannot remain beneath the die 4 like in FIG. 1. Instead the sample is surely guided towards a shaft tube 9, along which the sample falls into the vessel 8.

Figure 5:
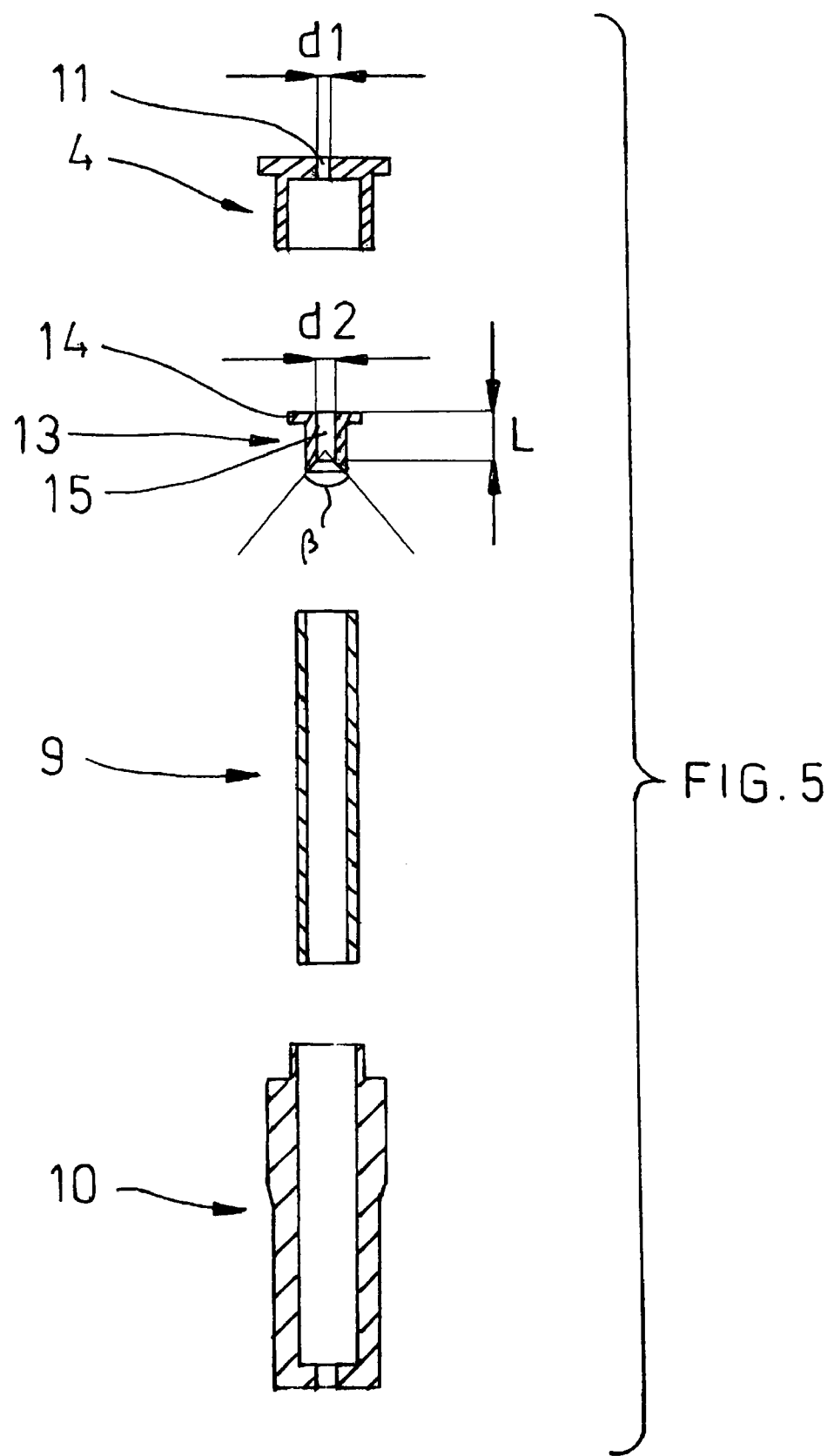
FIG. 5 shows the structure of the important parts of the punching tool according to FIG. 4 and illustrates the assembly thereof.

The structure of the guidance means 13 is illustrated in FIGS. 4 and 5. The guidance means 13 is formed of a part separate from the die 4. The die 4 is provided with a guidance channel 15, which forms an extension to a punching channel 11 in the die. The punching channel 11 and the guidance channel 15 are straight channels placed coaxially in line. A flange 14 on the upper surface of the guidance means 13 is placed between the die 4 and the shaft tube 9 so that the guidance means forms an extension to the die and the guidance channel 15 forms an extension to the punching channel 11. Differing from the embodiment shown in FIG. 4 the guidance means 13 may alternatively be integrated to the die itself so that the guidance channel forms an integral part with the die and representing the lower end of the die.

The diameter d2 of the guidance channel 15 in the guidance means 13 exceeds the diameter d1 of the punching channel 11 in the die 4 that is approximately 5 to 50 μm greater than the diameter d3 of the tip 6 of the punch. As a result of the above when the guidance means 13 is arranged against the lower end of the die 4, the guidance channel 15 forms at the connecting point with the punching channel 11 a dent or a shoulder 16, cf. the enlargement shown in FIG. 4. The shoulder 16 projects at least a distance S=10 μm from the surface of the guidance channel 15 towards the middle axis of the guidance channel, cf. the enlargement shown in FIG. 4. Preferably said distance S is at least 100 μm. The shoulder 16 is at an angle γ=90 degrees in relation to the longitudinal direction of the punching channel 11 of the die 4, whereby the walls of the shoulder are parallel, in other words at an angle 2γ=α=180 degrees in relation to one another. The angle γ may differ from the one shown in the Figure. Preferably the angle γ ranges from 85 to 150 degrees, in which case the angle α ranges from 170 to 300 degrees. The meaning of the shoulder 16 is that it prevents the fluffs of the punched sample 7 from drifting to the punching channel 11 of the die 4 when the punch 2 moves upwards in such a rare situation, in which the sample 7 has not been released from the punching tool as a result of the first stroke of the punch. When the punch 2 next strikes the sample in question, then said sample moves to the trailing end of the guidance means 13, where the inner diameter of the guidance means is significantly greater than diameter d2 of the guidance channel, and falls to the shaft tube 9. The diameter of the shaft tube 9 is at lest 3 mm, preferably 4 mm or greater than this, in which case it does not create an obstacle for the sample 7 when it falls.

If the angle γ concerned goes below 85 degrees, in other words α is below 170 degrees, then the shoulder 16 cannot adequately enough function as a stopping means for the fluffs of the sample 7.

In order that the sample would not in view of the release drift into an incorrect angle in the guidance channel 15, the diameter d2 thereof is preferably at the most the diameter d3 of the tip 6 of the punch added to the thickness of the filtering paper or another filtering material. Since the thickness of the filtering paper or some other filtering material is normally 0.2 to 1.0 mm and the diameter of the tip 6 of the punch is 0.2 to 2 mm, then it could roughly be estimated that the diameter d2 of the guidance channel 15 should be approximately 2× the diameter d3 of the tip 6 of the punch at the most. The guidance channel 15 allows the fluffs of the sample to collapse. Consequently the guidance channel 15 may be referred to as a tapering means. When the requirement set for the distance (width) S of the shoulder 16 is also taken into account, then the diameter d2 of the guidance channel 15 should be 1.02 to 2 (i.e. 1.02 . . . 2)× the diameter d3 of the tip 6 of the punch. It is to be recommended that the diameter d2 is 1.2 to 2 (i.e. 1.2 . . . 2)× the diameter d3 of the tip 6 of the punch. Dimensioning the length L of the portion provided with a standard diameter in the guidance channel 15 to be adequately long and the striking motion of the punch to be adequately powerful, it is ensured that the fluffs of the sample are not driven to the punching channel 11 of the die. It is to be recommended that the length L of the portion provided with a standard diameter in the guidance channel 15 is at least 2 mm. The length L is 5 mm in the example shown in the Figure.

FIG. 4 also shows that the guidance channel 15 in the guidance means 13 broadens towards the trailing end of the guidance means, i.e. the diameter of the guidance channel widens towards the free end of the guidance means 13, which is located opposite to the upper end pointing towards the die 4 of the guidance means. The trailing end of the guidance channel 15 is conically formed, while the cone angle β is 90 degrees. Technically the conical shape is easily achieved.

Owing to the cone angle β it is highly unlikely that the sample adheres to the lower end of the guidance means, since the fluffs in the sample do not adhere as easily to a broadened channel than to a narrow channel that ends at an angle β=180 degrees. The cone angle β may vary from the one shown in the Figure, preferably ranging within 50 and 100 degrees. If the cone angle β is small, i.e. below 50 degrees, then the guidance means 13 could become excessively long and it could also be possible for the sample to unnecessarily be guided back to the portion of the guidance channel 15 that is provided with a constant diameter. If the cone angle β is large, i.e. above approximately 100 degrees, then the guidance channel 15 is not capable of assigning/guiding the sample as reliably to the shaft tube 9 than if the cone angle were smaller than this. The guidance channel 15 may widen in another shape than the conical shape.

The cutting tip 6 of the punch is pushed in the lower position thereof past the lower end, or the free end, of the guidance means 13 and preferably an at least 2 mm distance, whereby the movement of the punch is highly reliably arranged to release the sample 7 with the fluffs thereof from the guidance means 13.

Preferably the quality of the surface in the guidance channel 15 of the guidance means 13 with the broadening diameters thereof is very good. Advantageously the smoothness of the surface in the guidance channel 15 corresponds to a polished surface, in which case the deviation of the surface roughness is preferably 0.4 μm. If the surface of the guidance channel is rough, it will not operate as desired. The guidance means 13 is preferably made of steel, and therefore at least the guidance channel 15 thereof including its broadenings are polished for the reason mentioned above.

The punching tool shown in FIG. 4 differs from the punching tool shown in FIG. 1 also in that the control part 3 of the punch is brought closer to the upper surface of the die 4. Owing to the above the tip 6 of the punch 2 is more accurately guided into the punching channel 11 of the die 4, thus improving the durability of the punch and the die.

The die 4 is preferably made of steel. The die 4 can be coated in order to improve the durability thereof. The coating may for instance be a diamond coating referred to as DIARC. Alternatively the coating may be made of for instance titanium nitride (TiN), titanium carbide (TiC) or titanium carbide nitride (TiCN).

FIGS. 6 to 9 illustrate the operation of the punching tool according to the invention.

FIG. 6 shows a situation, in which the tip 6 of the punch is brought against the upper surface of the filtering paper 5 and is moving downwards in order to perform the punching.

FIG. 7 shows a situation, in which the tip 6 of the punch has punched the sample 7 in one stroke from the filtering paper 5 so that the sample has fallen to the sample cup 8.

FIG. 8 illustrates a situation in which the first stroke of the punch 2 has released the sample 7 from the filtering paper 5, but the sample has not fallen to the sample cup 8, but as a result of the upwards directed return movement of the punch is adhered to the shoulder 16 formed by the guidance channel 15 of the guidance means 13 and the punching channel 11 of the die 4. The fluffs of the sample 7 keep the sample in this position. Since the recording device 10 of the punching tool has observed that the sample 7 has not been obtained as desired, the punch performs another stroke. FIG. 9 illustrates the effect of the new stroke of the punch 2. In FIG. 9 the punch 2 has by its downward movement released the sample 7 from the shoulder 16 and pushed the sample 7 along the guidance channel 15 so that it has fallen to the shaft tube 9, from where it falls to the sample cup 8. The release of the sample 7 is carried out by the guidance means, which provides the sample with a preferable position in the die/guidance means combination according to FIG. 8, from which position the sample is released when a new stroke is performed with the punch. The die/guidance means combination may provide the sample with other convenient positions deviating from those shown in FIG. 8, from where the sample also can be released as a result of a repeated stroke of the punch.

Above the invention has been described by means of one example and therefore it is pointed out that for those skilled in the art it is obvious that the details of the invention can be implemented in various ways within the scope of the accompanying claims. Thus, for instance the diameter of the punch need not be circular but may for example be oval. However, the circular diameter is preferable for manufactural reasons. It is conceivable that a small gap is placed between the guidance channel 15 of the guidance means 13 and the lower side of the punching channel 11 of the die 4, in other words at the shoulder 16.

The invention claimed is:

1. A punching tool for taking a biological sample from a filter, the punching tool comprising:
   a punch;
   a die providing a punching channel for receiving the punch and the biological sample and for conveying the biological sample from an upper surface of the die to a lower end of the die; and
   a guidance means arranged against the lower end of the die, the guidance means comprising a guidance channel arranged coaxially with the punching channel of the die to form an extension of the punching channel of the die for further receiving the biological sample from the punching channel of the die, the diameter of the guidance channel exceeding the diameter of the punching channel of the die at a connection point of the guidance means to the die, the guidance channel forming a shoulder at a connection point that connects the guidance channel to the punching channel of the die.

2. A punching tool as claimed in claim 1, wherein the diameter of the guidance channel in the guidance means is constant for a length of at least 2 mm of the guidance channel from the connection point.

3. A punching tool as claimed in claim 2, wherein the cross section of the guidance channel in the guidance means is circular.

4. A punching tool as claimed in claim 2, wherein a tip of the punch is arranged to be moved a distance of at least 2 mm past a free end of the guidance means that is opposite the connection point.

5. A punching tool as claimed in claim 1, wherein the diameter of the guidance channel in the guidance means is 1.2 to 2 times the diameter of the punch.

6. A punching tool as claimed in claim 5, wherein the cross section of the guidance channel in the guidance means is circular.

7. A punching tool as claimed in claim 6, wherein the guidance channel conically widens at a free end of the guidance means that is opposite the connection point.

8. A punching tool as claimed in claim 7, wherein a tip of the punch is arranged to be moved a distance of at least 2 mm past the free end of the guidance means.

9. A punching tool as claimed in claim 7, wherein the cone angle of the guidance channel in the guidance means ranges from 50 to 100 degrees.

10. A punching tool as claimed in claim 9, wherein a tip of the punch is arranged to be moved a distance of at least 2 mm past the free end of the guidance means.

11. A punching tool as claimed in claim 5, wherein a tip of the punch is arranged to be moved a distance of at least 2 mm past a free end of the guidance means that is opposite the connection point.

12. A punching tool as claimed in claim 1, wherein the cross section of the guidance channel in the guidance means is circular.

13. A punching tool as claimed in claim 12, wherein a tip of the punch is arranged to be moved a distance of at least 2 mm past a free end of the guidance means that is opposite the connection point.

14. A punching tool as claimed in claim 1, wherein the guidance channel in the guidance means is polished.

15. A punching tool as claimed in claim 14, wherein a tip of the punch is arranged to be moved a distance of at least 2 mm past a free end of the guidance means that is opposite the connection point.

16. A punching tool as claimed in claim 1, wherein the walls of the shoulder are placed at an angle ranging from 180 to 300 degrees in relation to one another.

17. A punching tool as claimed in claim 1, wherein a tip of the punch is arranged to be moved a distance of at least 2 mm past a free end of the guidance means that is opposite the connection point.

18. A punching tool as claimed in claim 1, wherein the guidance means is arranged inside a shaft tube, the diameter of the shaft tube being at least 3 mm.

19. A punching tool as claimed in claim 1, wherein the guidance means is an element separate from the die.

20. A punching tool as claimed in claim 1, wherein the guidance channel in the guidance means is connected to the punching channel of the die without clearance.

* * * * *